United States Patent
Li et al.

(10) Patent No.: US 11,382,751 B2
(45) Date of Patent: Jul. 12, 2022

(54) SELF-EXPANDABLE FILLER FOR MITIGATING PARAVALVULAR LEAK

(71) Applicant: St. Jude Medical, Cardiology Division, Inc., St. Paul, MN (US)

(72) Inventors: Xue Mei Li, Shoreview, MN (US); Michael P. Meyer, Minnetrista, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 50 days.

(21) Appl. No.: 16/162,532

(22) Filed: Oct. 17, 2018

(65) Prior Publication Data
US 2019/0117387 A1    Apr. 25, 2019

Related U.S. Application Data

(60) Provisional application No. 62/576,204, filed on Oct. 24, 2017.

(51) Int. Cl.
*A61F 2/24* (2006.01)
*A61F 2/90* (2013.01)

(52) U.S. Cl.
CPC ............ *A61F 2/246* (2013.01); *A61F 2/2418* (2013.01); *A61F 2/24* (2013.01); *A61F 2/2445* (2013.01); *A61F 2/90* (2013.01); *A61F 2210/0076* (2013.01); *A61F 2250/0039* (2013.01); *A61F 2250/0069* (2013.01)

(58) Field of Classification Search
CPC ........................................................ A61F 2/24
See application file for complete search history.

(56) References Cited

U.S. PATENT DOCUMENTS

| 3,657,744 A | 4/1972 | Ersek |
| 4,275,469 A | 6/1981 | Gabbay |

(Continued)

FOREIGN PATENT DOCUMENTS

| DE | 19857887 A1 | 7/2000 |
| DE | 10121210 A1 | 11/2002 |

(Continued)

OTHER PUBLICATIONS

Ruiz, Carlos, Overview of PRE-CE Mark Transcatheter Aortic Valve Technologies, Euro PCR—dated May 25, 2010.

(Continued)

*Primary Examiner* — Jacqueline Woznicki
(74) *Attorney, Agent, or Firm* — Wei & Sleman LLP (57) ABSTRACT

A prosthetic heart valve includes a collapsible stent and a valve assembly disposed within the stent. A first cuff is disposed adjacent the stent. A filler is annularly disposed about the stent radially outward of the first cuff and radially outward of the stent. The filler has a first circumferential layer with a first inner wall, a first outer wall, and a plurality of first ribs connecting the first inner wall to the first outer wall. The filler has an expanded condition in which the first inner wall is spaced a first distance from the first outer wall in a radial direction transverse to the longitudinal direction of the stent, and a collapsed condition in which the first inner wall is spaced a second distance from the first outer wall in the radial direction, the first distance being greater than the second distance.

16 Claims, 6 Drawing Sheets

(56) References Cited

U.S. PATENT DOCUMENTS

| | | | |
|---|---|---|---|
| 4,491,986 | A | 1/1985 | Gabbay |
| 4,759,758 | A | 7/1988 | Gabbay |
| 4,878,906 | A | 11/1989 | Lindemann et al. |
| 4,922,905 | A | 5/1990 | Strecker |
| 4,994,077 | A | 2/1991 | Dobben |
| 5,163,955 | A * | 11/1992 | Love ............ A61F 2/2412 623/2.15 |
| 5,258,023 | A * | 11/1993 | Reger ........... A61F 2/2409 623/2.18 |
| 5,411,552 | A | 5/1995 | Andersen et al. |
| 5,415,664 | A | 5/1995 | Pinchuk |
| 5,480,423 | A | 1/1996 | Ravenscroft et al. |
| 5,755,783 | A * | 5/1998 | Stobie ........... A61F 2/2409 623/2.39 |
| 5,843,167 | A | 12/1998 | Dwyer et al. |
| 5,855,601 | A | 1/1999 | Bessler et al. |
| 5,935,163 | A | 8/1999 | Gabbay |
| 5,961,549 | A | 10/1999 | Nguyen et al. |
| 6,045,576 | A * | 4/2000 | Starr ............. A61F 2/2409 623/2.41 |
| 6,077,297 | A | 6/2000 | Robinson et al. |
| 6,083,257 | A | 7/2000 | Taylor et al. |
| 6,090,140 | A | 7/2000 | Gabbay |
| 6,214,036 | B1 | 4/2001 | Letendre et al. |
| 6,264,691 | B1 | 7/2001 | Gabbay |
| 6,267,783 | B1 | 7/2001 | Letendre et al. |
| 6,368,348 | B1 | 4/2002 | Gabbay |
| 6,371,983 | B1 * | 4/2002 | Lane ............. A61F 2/2409 623/2.14 |
| 6,419,695 | B1 | 7/2002 | Gabbay |
| 6,425,916 | B1 * | 7/2002 | Garrison ........ A61F 2/2418 623/1.26 |
| 6,458,153 | B1 | 10/2002 | Bailey et al. |
| 6,468,660 | B2 | 10/2002 | Ogle et al. |
| 6,488,702 | B1 | 12/2002 | Besselink |
| 6,517,576 | B2 | 2/2003 | Gabbay |
| 6,533,810 | B2 | 3/2003 | Hankh et al. |
| 6,582,464 | B2 | 6/2003 | Gabbay |
| 6,610,088 | B1 | 8/2003 | Gabbay |
| 6,623,518 | B2 | 9/2003 | Thompson et al. |
| 6,652,578 | B2 | 11/2003 | Bailey et al. |
| 6,685,625 | B2 | 2/2004 | Gabbay |
| 6,716,244 | B2 | 4/2004 | Klaco |
| 6,719,789 | B2 | 4/2004 | Cox |
| 6,730,118 | B2 | 5/2004 | Spenser et al. |
| 6,783,556 | B1 | 8/2004 | Gabbay |
| 6,790,230 | B2 | 9/2004 | Beyersdorf et al. |
| 6,814,746 | B2 | 11/2004 | Thompson et al. |
| 6,830,584 | B1 | 12/2004 | Seguin |
| 6,869,444 | B2 | 3/2005 | Gabbay |
| 6,893,460 | B2 | 5/2005 | Spenser et al. |
| 6,908,481 | B2 | 6/2005 | Cribier |
| 6,951,573 | B1 | 10/2005 | Dilling |
| 7,018,406 | B2 | 3/2006 | Seguin et al. |
| 7,025,780 | B2 | 4/2006 | Gabbay |
| 7,137,184 | B2 | 11/2006 | Schreck |
| 7,160,322 | B2 | 1/2007 | Gabbay |
| 7,195,641 | B2 | 3/2007 | Palmaz et al. |
| 7,247,167 | B2 | 7/2007 | Gabbay |
| 7,267,686 | B2 | 9/2007 | DiMatteo et al. |
| 7,276,078 | B2 | 10/2007 | Spenser et al. |
| 7,311,730 | B2 | 12/2007 | Gabbay |
| 7,320,704 | B2 | 1/2008 | Lashinski et al. |
| 7,329,278 | B2 | 2/2008 | Seguin et al. |
| 7,374,573 | B2 | 5/2008 | Gabbay |
| 7,381,218 | B2 | 6/2008 | Schreck |
| 7,381,219 | B2 | 6/2008 | Salahieh et al. |
| 7,452,371 | B2 | 11/2008 | Pavcnik et al. |
| 7,510,572 | B2 | 3/2009 | Gabbay |
| 7,510,575 | B2 | 3/2009 | Spenser et al. |
| 7,524,331 | B2 | 4/2009 | Birdsall |
| 7,534,261 | B2 | 5/2009 | Friedman |
| RE40,816 | E | 6/2009 | Taylor et al. |
| 7,585,321 | B2 | 9/2009 | Cribier |
| 7,628,805 | B2 | 12/2009 | Spenser et al. |
| 7,682,390 | B2 | 3/2010 | Seguin |
| 7,708,775 | B2 | 5/2010 | Rowe et al. |
| 7,731,742 | B2 | 6/2010 | Schlick et al. |
| 7,748,389 | B2 | 7/2010 | Salahieh et al. |
| 7,780,725 | B2 | 8/2010 | Haug et al. |
| 7,799,069 | B2 | 9/2010 | Bailey et al. |
| 7,803,185 | B2 | 9/2010 | Gabbay |
| 7,824,442 | B2 | 11/2010 | Salahieh et al. |
| 7,837,727 | B2 | 11/2010 | Goetz et al. |
| 7,846,203 | B2 | 12/2010 | Cribier |
| 7,846,204 | B2 | 12/2010 | Letac et al. |
| 7,857,845 | B2 | 12/2010 | Stacchino et al. |
| 7,892,281 | B2 | 2/2011 | Seguin et al. |
| 7,914,569 | B2 | 3/2011 | Nguyen et al. |
| 7,959,666 | B2 | 6/2011 | Salahieh et al. |
| 7,959,672 | B2 | 6/2011 | Salahieh et al. |
| 7,972,378 | B2 | 7/2011 | Tabor et al. |
| 7,988,724 | B2 | 8/2011 | Salahieh et al. |
| 7,993,394 | B2 | 8/2011 | Hariton et al. |
| 8,016,877 | B2 | 9/2011 | Seguin et al. |
| D648,854 | S | 11/2011 | Braido |
| 8,048,153 | B2 | 11/2011 | Salahieh et al. |
| 8,052,741 | B2 | 11/2011 | Bruszewski et al. |
| 8,052,749 | B2 | 11/2011 | Salahieh et al. |
| 8,052,750 | B2 | 11/2011 | Tuval et al. |
| 8,062,355 | B2 | 11/2011 | Figulla et al. |
| 8,075,611 | B2 | 12/2011 | Millwee et al. |
| D652,926 | S | 1/2012 | Braido |
| D652,927 | S | 1/2012 | Braido et al. |
| D653,341 | S | 1/2012 | Braido et al. |
| D653,342 | S | 1/2012 | Braido et al. |
| D653,343 | S | 1/2012 | Ness et al. |
| D654,169 | S | 2/2012 | Braido |
| D654,170 | S | 2/2012 | Braido et al. |
| 8,137,398 | B2 | 3/2012 | Tuval et al. |
| 8,142,497 | B2 | 3/2012 | Friedman |
| D660,432 | S | 5/2012 | Braido |
| D660,433 | S | 5/2012 | Braido et al. |
| D660,967 | S | 5/2012 | Braido et al. |
| 8,167,936 | B2 * | 5/2012 | Kurian ........... A61F 2/2427 623/2.41 |
| 8,182,528 | B2 | 5/2012 | Salahieh et al. |
| 8,221,493 | B2 | 7/2012 | Boyle et al. |
| 8,230,717 | B2 | 7/2012 | Matonick |
| 8,231,670 | B2 | 7/2012 | Salahieh et al. |
| 8,252,051 | B2 | 8/2012 | Chau et al. |
| 8,257,434 | B2 * | 9/2012 | Matheny ........ A61F 2/2412 623/2.19 |
| 8,308,798 | B2 | 11/2012 | Pintor et al. |
| 8,313,525 | B2 | 11/2012 | Tuval et al. |
| 8,323,335 | B2 | 12/2012 | Rowe et al. |
| 8,323,336 | B2 | 12/2012 | Hill et al. |
| 8,343,213 | B2 | 1/2013 | Salahieh et al. |
| 8,348,995 | B2 | 1/2013 | Tuval et al. |
| 8,348,996 | B2 | 1/2013 | Tuval et al. |
| 8,348,998 | B2 | 1/2013 | Pintor et al. |
| 8,366,769 | B2 * | 2/2013 | Huynh ........... A61F 2/2409 623/2.41 |
| 8,403,983 | B2 | 3/2013 | Quadri et al. |
| 8,408,214 | B2 | 4/2013 | Spenser |
| 8,414,643 | B2 | 4/2013 | Tuval et al. |
| 8,425,593 | B2 | 4/2013 | Braido et al. |
| 8,449,599 | B2 | 5/2013 | Chau et al. |
| 8,449,604 | B2 | 5/2013 | Moaddeb et al. |
| D684,692 | S | 6/2013 | Braido |
| 8,454,686 | B2 | 6/2013 | Alkhatib |
| 8,500,798 | B2 | 8/2013 | Rowe et al. |
| 8,568,474 | B2 | 10/2013 | Yeung et al. |
| 8,579,962 | B2 | 11/2013 | Salahieh et al. |
| 8,579,966 | B2 | 11/2013 | Seguin et al. |
| 8,585,755 | B2 | 11/2013 | Chau et al. |
| 8,591,575 | B2 | 11/2013 | Cribier |
| 8,597,349 | B2 | 12/2013 | Alkhatib |
| 8,603,159 | B2 | 12/2013 | Seguin et al. |
| 8,603,160 | B2 | 12/2013 | Salahieh et al. |
| 8,613,765 | B2 | 12/2013 | Bonhoeffer et al. |
| 8,623,074 | B2 | 1/2014 | Ryan |
| 8,652,204 | B2 | 2/2014 | Quill et al. |

(56) References Cited

U.S. PATENT DOCUMENTS

| | | | |
|---|---|---|---|
| 8,663,322 B2 | 3/2014 | Keranen | |
| 8,668,733 B2 | 3/2014 | Haug et al. | |
| 8,685,080 B2 | 4/2014 | White | |
| 8,728,154 B2 | 5/2014 | Alkhatib | |
| 8,747,459 B2 | 6/2014 | Nguyen et al. | |
| 8,764,820 B2 | 7/2014 | Dehdashtian et al. | |
| 8,795,357 B2 | 8/2014 | Yohanan et al. | |
| 8,801,776 B2 | 8/2014 | House et al. | |
| 8,808,356 B2 | 8/2014 | Braido et al. | |
| 8,828,078 B2 | 9/2014 | Salahieh et al. | |
| 8,834,563 B2 | 9/2014 | Righini | |
| 8,840,661 B2 | 9/2014 | Manasse | |
| 8,840,663 B2 | 9/2014 | Salahieh et al. | |
| 8,876,894 B2 | 11/2014 | Tuval et al. | |
| 8,876,895 B2 | 11/2014 | Tuval et al. | |
| 8,940,040 B2 | 1/2015 | Shahriari | |
| 8,945,209 B2 | 2/2015 | Bonyuet et al. | |
| 8,961,595 B2 | 2/2015 | Alkhatib | |
| 8,974,523 B2 | 3/2015 | Thill et al. | |
| 8,974,524 B2 | 3/2015 | Yeung et al. | |
| 9,220,594 B2 * | 12/2015 | Braido | A61F 2/2418 |
| 9,326,856 B2 * | 5/2016 | Schraut | A61F 2/2418 |
| 9,398,951 B2 * | 7/2016 | Alkhatib | A61F 2/2418 |
| 9,532,868 B2 * | 1/2017 | Braido | A61F 2/2418 |
| 9,668,858 B2 * | 6/2017 | Morin | A61F 2/2418 |
| 9,757,230 B2 * | 9/2017 | Fahim | A61F 2/2418 |
| 9,820,852 B2 * | 11/2017 | Braido | A61F 2/2403 |
| 10,143,551 B2 * | 12/2018 | Braido | A61F 2/2436 |
| 10,271,949 B2 * | 4/2019 | Dakin | A61F 2/2418 |
| 10,321,991 B2 * | 6/2019 | Glimsdale | A61F 2/2418 |
| 2002/0036220 A1 | 3/2002 | Gabbay | |
| 2003/0023303 A1 | 1/2003 | Palmaz et al. | |
| 2003/0050694 A1 | 3/2003 | Yang et al. | |
| 2003/0130726 A1 | 7/2003 | Thorpe et al. | |
| 2004/0049262 A1 | 3/2004 | Obermiller et al. | |
| 2004/0093075 A1 | 5/2004 | Kuehne | |
| 2004/0111111 A1 | 6/2004 | Lin | |
| 2004/0210304 A1 | 10/2004 | Seguin et al. | |
| 2004/0260389 A1 | 12/2004 | Case et al. | |
| 2005/0096726 A1 | 5/2005 | Sequin et al. | |
| 2005/0137682 A1 | 6/2005 | Justino | |
| 2005/0137695 A1 | 6/2005 | Salahieh et al. | |
| 2005/0137697 A1 | 6/2005 | Salahieh et al. | |
| 2005/0203605 A1 | 9/2005 | Dolan | |
| 2005/0240200 A1 | 10/2005 | Bergheim | |
| 2005/0256566 A1 | 11/2005 | Gabbay | |
| 2006/0008497 A1 | 1/2006 | Gabbay | |
| 2006/0074484 A1 | 4/2006 | Huber | |
| 2006/0122692 A1 | 6/2006 | Gilad et al. | |
| 2006/0149360 A1 | 7/2006 | Schwammenthal et al. | |
| 2006/0161249 A1 | 7/2006 | Realyvasquez et al. | |
| 2006/0173532 A1 | 8/2006 | Flagle et al. | |
| 2006/0178740 A1 | 8/2006 | Stacchino et al. | |
| 2006/0195180 A1 | 8/2006 | Kheradvar et al. | |
| 2006/0206202 A1 | 9/2006 | Bonhoeffer et al. | |
| 2006/0241744 A1 | 10/2006 | Beith | |
| 2006/0241745 A1 | 10/2006 | Solem | |
| 2006/0259120 A1 | 11/2006 | Vongphakdy et al. | |
| 2006/0259137 A1 * | 11/2006 | Artof | A61F 2/243 623/2.18 |
| 2006/0265056 A1 | 11/2006 | Nguyen et al. | |
| 2006/0276813 A1 | 12/2006 | Greenberg | |
| 2006/0276874 A1 | 12/2006 | Wilson et al. | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0067029 A1 | 3/2007 | Gabbay | |
| 2007/0093890 A1 | 4/2007 | Eliasen et al. | |
| 2007/0100435 A1 | 5/2007 | Case et al. | |
| 2007/0118210 A1 | 5/2007 | Pinchuk | |
| 2007/0213813 A1 | 9/2007 | Von Segesser et al. | |
| 2007/0233228 A1 | 10/2007 | Eberhardt et al. | |
| 2007/0244545 A1 | 10/2007 | Birdsall et al. | |
| 2007/0244552 A1 | 10/2007 | Salahieh et al. | |
| 2007/0288087 A1 | 12/2007 | Fearnot et al. | |
| 2008/0021552 A1 | 1/2008 | Gabbay | |
| 2008/0039934 A1 | 2/2008 | Styrc | |
| 2008/0071369 A1 | 3/2008 | Tuval et al. | |
| 2008/0082164 A1 | 4/2008 | Friedman | |
| 2008/0097595 A1 | 4/2008 | Gabbay | |
| 2008/0114452 A1 | 5/2008 | Gabbay | |
| 2008/0125853 A1 | 5/2008 | Bailey et al. | |
| 2008/0140189 A1 | 6/2008 | Nguyen et al. | |
| 2008/0147183 A1 | 6/2008 | Styrc | |
| 2008/0154355 A1 | 6/2008 | Benichou et al. | |
| 2008/0154356 A1 | 6/2008 | Obermiller et al. | |
| 2008/0243245 A1 | 10/2008 | Thambar et al. | |
| 2008/0255662 A1 | 10/2008 | Stacchino et al. | |
| 2008/0262602 A1 | 10/2008 | Wilk et al. | |
| 2008/0269879 A1 | 10/2008 | Sathe et al. | |
| 2009/0099653 A1 | 4/2009 | Suri et al. | |
| 2009/0112309 A1 | 4/2009 | Jaramillo et al. | |
| 2009/0138079 A1 | 5/2009 | Tuval et al. | |
| 2009/0276027 A1 | 11/2009 | Glynn | |
| 2010/0004740 A1 | 1/2010 | Seguin et al. | |
| 2010/0036484 A1 | 2/2010 | Hariton et al. | |
| 2010/0049306 A1 | 2/2010 | House et al. | |
| 2010/0087907 A1 | 4/2010 | Lattouf | |
| 2010/0131055 A1 | 5/2010 | Case et al. | |
| 2010/0168778 A1 | 7/2010 | Braido | |
| 2010/0168839 A1 | 7/2010 | Braido et al. | |
| 2010/0168844 A1 | 7/2010 | Toomes et al. | |
| 2010/0185277 A1 | 7/2010 | Braido et al. | |
| 2010/0191326 A1 | 7/2010 | Alkhatib | |
| 2010/0204781 A1 | 8/2010 | Alkhatib | |
| 2010/0204785 A1 | 8/2010 | Alkhatib | |
| 2010/0217382 A1 | 8/2010 | Chau et al. | |
| 2010/0234940 A1 | 9/2010 | Dolan | |
| 2010/0249911 A1 | 9/2010 | Alkhatib | |
| 2010/0249923 A1 | 9/2010 | Alkhatib et al. | |
| 2010/0286768 A1 | 11/2010 | Alkhatib | |
| 2010/0298931 A1 | 11/2010 | Quadri et al. | |
| 2011/0029072 A1 | 2/2011 | Gabbay | |
| 2011/0054466 A1 | 3/2011 | Rothstein et al. | |
| 2011/0098800 A1 | 4/2011 | Braido et al. | |
| 2011/0098802 A1 | 4/2011 | Braido et al. | |
| 2011/0137397 A1 | 6/2011 | Chau et al. | |
| 2011/0172765 A1 | 7/2011 | Nguyen et al. | |
| 2011/0208283 A1 | 8/2011 | Rust | |
| 2011/0264206 A1 | 10/2011 | Tabor | |
| 2012/0035722 A1 | 2/2012 | Tuval | |
| 2012/0059458 A1 * | 3/2012 | Buchbinder | A61F 2/2409 623/2.36 |
| 2012/0071969 A1 * | 3/2012 | Li | A61F 2/2418 623/2.17 |
| 2012/0078347 A1 | 3/2012 | Braido et al. | |
| 2012/0078352 A1 | 3/2012 | Wang et al. | |
| 2012/0101572 A1 | 4/2012 | Kovalsky et al. | |
| 2012/0123529 A1 | 5/2012 | Levi et al. | |
| 2012/0303116 A1 | 11/2012 | Gorman, III et al. | |
| 2013/0274873 A1 | 10/2013 | Delaloye et al. | |
| 2014/0005778 A1 * | 1/2014 | Buchbinder | A61F 2/2412 623/2.18 |
| 2014/0121763 A1 | 5/2014 | Duffy et al. | |
| 2014/0155997 A1 | 6/2014 | Braido | |
| 2014/0214159 A1 | 7/2014 | Vidlund et al. | |
| 2014/0228946 A1 | 8/2014 | Chau et al. | |
| 2014/0303719 A1 | 10/2014 | Cox et al. | |
| 2014/0324164 A1 | 10/2014 | Gross et al. | |
| 2014/0343671 A1 | 11/2014 | Yohanan et al. | |
| 2014/0350668 A1 | 11/2014 | Delaloye et al. | |
| 2014/0350669 A1 | 11/2014 | Gillespie et al. | |
| 2018/0055631 A1 | 3/2018 | Morin et al. | |
| 2018/0116798 A1 | 5/2018 | Perszyk | |

FOREIGN PATENT DOCUMENTS

| | | |
|---|---|---|
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1584306 A1 | 10/2005 |
| EP | 1598031 A2 | 11/2005 |

(56) References Cited

FOREIGN PATENT DOCUMENTS

| | | | |
|---|---|---|---|
| EP | 1360942 | B1 | 12/2005 |
| EP | 1926455 | A2 | 6/2008 |
| EP | 2537487 | A1 | 12/2012 |
| FR | 2850008 | A1 | 7/2004 |
| FR | 2847800 | B1 | 10/2005 |
| WO | 9117720 | A1 | 11/1991 |
| WO | 9716133 | A1 | 5/1997 |
| WO | 9832412 | A2 | 7/1998 |
| WO | 9913801 | A1 | 3/1999 |
| WO | 01028459 | A1 | 4/2001 |
| WO | 0149213 | A2 | 7/2001 |
| WO | 01054625 | A1 | 8/2001 |
| WO | 01056500 | A2 | 8/2001 |
| WO | 01076510 | A2 | 10/2001 |
| WO | 0236048 | A1 | 5/2002 |
| WO | 0247575 | A2 | 6/2002 |
| WO | 02067782 | A2 | 9/2002 |
| WO | 03047468 | A1 | 6/2003 |
| WO | 2005070343 | A1 | 8/2005 |
| WO | 06073626 | A2 | 7/2006 |
| WO | 2007053243 | A2 | 5/2007 |
| WO | 07071436 | A2 | 6/2007 |
| WO | 08070797 | A2 | 6/2008 |
| WO | 10008548 | A2 | 1/2010 |
| WO | 10008549 | A1 | 1/2010 |
| WO | 10096176 | A1 | 8/2010 |
| WO | 10098857 | A1 | 9/2010 |

OTHER PUBLICATIONS

Percutaneous aortic valve replacement: resection before implantation, 836-840, Quaden, Rene et al., European J. of Cardio-thoracic Surgery, 27 (2005).

Catheter-implanted prosthetic heart valves, Knudsen, L.L., et al., The International Journal of Artificial Organs, vol. 16, No. 5 1993, pp. 253-262.

Transluminal Aortic Valve Placement, Moazami, Nader, et al., ASAIO Journal, 1996; 42:M381-M385.

Transluminal Catheter Implanted Prosthetic Heart Valves, Andersen, Henning Rud, International Journal of Angiology 7:102-106 (1998).

Transluminal implantation of artificial heart valves, Andersen, H. R., et al., European Heart Journal (1992) 13, 704-708.

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

"Direct-Access Valve Replacement", Christoph H. Huber, et al., Journal of the American College of Cardiology, vol. 46, No. 2, (Jul. 19, 2005).

"Percutaneous Aortic Valve Implantation Retrograde From the Femoral Artery", John G. Webb et al., Circulation, 2006; 113:842-850 (Feb. 6, 2006).

"Minimally invasive cardiac surgery", M. J. Mack, Surgical Endoscopy, 2006, 20:S488-S492, DOI: 10.1007/s00464-006-0110-8 (presented Apr. 24, 2006).

"Transapical Transcatheter Aortic Valve Implantation in Humans", Samuel V. Lichtenstein et al., Circulation. 2006; 114: 591-596 (Jul. 31, 2006).

"Closed heart surgery: Back to the future", Samuel V. Lichtenstein, The Journal of Thoracic and Cardiovascular Surgery, vol. 131, No. 5, pp. 941-943.

"Transapical approach for sutureless stent-fixed aortic valve implantation: experimental results"; Th. Walther et al., European Journal of Cardio-thoracic Surgery 29 (2006) 703-708 (Jan. 30, 2006).

"Transapical aortic valve implantation: an animal feasibility study"; Todd M. Dewey et al., The annals of thoracic surgery 2006; 82: 110-6 (Feb. 13, 2006).

Textbook "Transcatheter Valve Repair", 2006, pp. 165-186.

Rohde, I., Masch, J.-M., Theisen-Kunde, D., Marczynski-Bühlow, M., Bombien Quaden, R., Lutter, G. and Brinkmann, R. (2015), Resection of Calcified Aortic Heart Leaflets In Vitro by Q-Switched 2?μm Microsecond Laser Radiation. Journal of Cardiac Surgery, 30: 157-162. doi: 10.1111/jocs.12481.

Muñoz, Daniel Rodríguez, Carla Lázaro Rivera, and José Luis Zamorano Gómez. "Guidance of treatment of perivalvular prosthetic leaks." Current cardiology reports 16.1 (2014): 1-6.

Gössl, Mario, and Charanjit S. Rihal. "Percutaneous treatment of aortic and mitral valve paravalvular regurgitation." Current cardiology reports 15.8 (2013): 1-8.

Swiatkiewicz, Iwona, et al. "Percutaneous closure of mitral perivalvular leak." Kardiologia polska 67.7 (2009): 762.

De Cicco, Giuseppe, et al. "Aortic valve periprosthetic leakage: anatomic observations and surgical results." The Annals of thoracic surgery 79.5 (2005): 1480-1485.

Heat Advisor, "Heart repairs without surgery. Minimally invasive procedures aim to correct valve leakage", Sep. 2004, PubMed ID 15586429.

Transcatheter Umbrella Closure of Valvular and Paravalvular Leaks, Hourihan et al., Journal of the American College of Cardiology, vol. 20, No. 6, pp. 1371-1377, (1992).

Buellesfeld et al., Treatment of paravalvular leaks through inverventional techniques; Department of Cardiology, Ben University Hospital 2011.

* cited by examiner

SELF-EXPANDABLE FILLER FOR MITIGATING PARAVALVULAR LEAK

CROSS-REFERENCE TO RELATED APPLICATIONS

This application claims the benefit of the filing date of U.S. Provisional Patent Application No. 62/576,204, filed Oct. 24, 2017, the disclosure of which is hereby incorporated by reference herein.

BACKGROUND OF THE DISCLOSURE

The present disclosure relates to heart valve replacement and, in particular, to collapsible prosthetic heart valves. More particularly, the present disclosure relates to collapsible prosthetic transcatheter heart valves that minimize or reduce paravalvular leaks.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are ordinarily mounted: a self-expanding stent and a balloon-expandable stent. To load such valves into a delivery apparatus and deliver them into a patient, the valve is first collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the valve, assuring its proper location, and then expanding a balloon positioned within the valve stent. For self-expanding valves, on the other hand, the stent automatically expands as a sheath covering the valve is withdrawn.

After implantation, imperfect sealing between the prosthetic valve and the native tissue at the site of implantation may cause complications such as paravalvular leakage ("PV leak") in which retrograde blood flows through one or more gaps formed between the structure of the implanted valve and cardiac tissue as a result of the imperfect sealing.

BRIEF SUMMARY

According to one aspect of the disclosure, a prosthetic heart valve for replacing a native valve includes a stent, a valve assembly, a first cuff, and a filler. The stent extends in a longitudinal direction from an inflow end to an outflow end and has a plurality of stent cells formed by struts, a collapsed condition and an expanded condition. The valve assembly is disposed within the stent. The first cuff is annularly disposed adjacent the stent. The filler is annularly disposed about the stent radially outward of the first cuff and radially outward of the stent. The filler has a first circumferential layer with a first inner wall, a first outer wall, and a plurality of first ribs connecting the first inner wall to the first outer wall. The filler has an expanded condition in which the first inner wall is spaced a first distance from the first outer wall in a radial direction transverse to the longitudinal direction of the stent, and a collapsed condition in which the first inner wall is spaced a second distance from the first outer wall in the radial direction. The first distance is greater than the second distance

BRIEF DESCRIPTION OF THE DRAWINGS

Various embodiments of the presently disclosed prosthetic heart valve may be more fully understood with reference to the following detailed description when read with the accompanying drawings, in which.

DETAILED DESCRIPTION

As used herein in connection with a prosthetic heart valve, the term "inflow end" refers to the end of the heart valve through which blood enters when the valve is functioning as intended, and the term "outflow end" refers to the end of the heart valve through which blood exits when the valve is functioning as intended. As used herein, the term "proximal" refers to the inflow end of a prosthetic heart valve or to elements of a prosthetic heart valve that are relatively close to the inflow end, and the term "distal" refers to the outflow end of a prosthetic heart valve or to elements of a prosthetic heart valve that are relatively close to the outflow end. As used herein, the terms "generally," "substantially," and "about" are intended to mean that slight deviations from absolute are included within the scope of the term so modified. Like numbers refer to similar or identical elements throughout. When used herein in the context of a prosthetic heart valve, or a component thereof, the lengthwise or axial direction refers to a direction parallel to a longitudinal axis passing through the center of the stent or heart valve from the inflow end to the outflow end. When used herein in the context of a prosthetic heart valve, or a component thereof, the circumferential direction refers to a direction extending along the circumference of the prosthetic heart valve.

Figure 1:
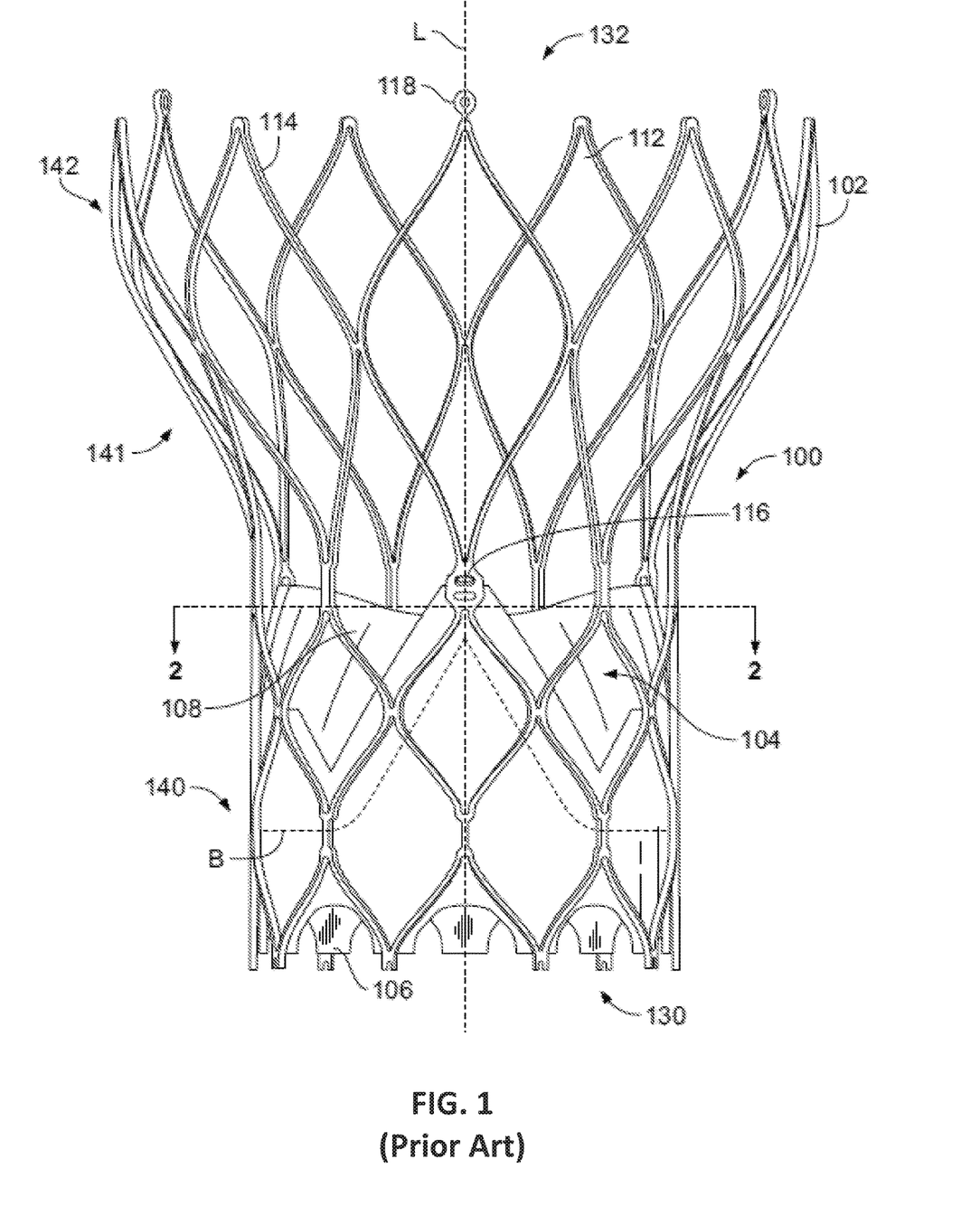
FIG. 1 is a front view of a collapsible prosthetic heart valve according to the prior art, shown in an expanded condition.

FIG. 1 shows a collapsible stent-supported prosthetic heart valve 100 according to the prior art, the prosthetic heart valve being shown in an expanded condition. Prosthetic heart valve 100 is designed to replace the function of the native aortic valve of a patient. Prosthetic heart valve 100 includes a stent 102 which serves as a frame for the valve elements. Stent 102 extends along a lengthwise or longitudinal axis L from an inflow or annulus end 130 to an outflow or aortic end 132, and includes an annulus section 140 adjacent inflow end 130 and an aortic section 142 adjacent outflow end 132. Annulus section 140 may be in the form of a cylinder having a substantially constant diameter along its length, and may have a relatively small transverse cross-section in the expanded condition in comparison to the transverse cross-section of aortic section 142. A transition section 141 may taper outwardly from annulus section 140 to aortic section 142. Each of the sections of stent 102 includes a plurality of cells 112 formed by interconnected struts 114. Each cell 112 may include four struts 114 connected together generally in a diamond shape so as to form a cell that may be readily collapsed and expanded. It will be appreciated that a smaller or larger number of struts may be used to form cells having a different shape. The cells 112 in each section of stent 102 may be connected to one another in one or more annular rows around the stent. For example, as shown in FIG. 1, annulus section 140 may have two annular rows of complete cells 112, with the cells in one annular row offset by one-half cell width in the circumferential direction from the cells in the other annular row. Aortic section 142 and transition section 141 may each have one or more annular rows of complete or partial cells 112. The cells in aortic section 142 may be larger than the cells in annulus section 140 so as to better enable prosthetic valve 100 to be positioned within the aortic annulus without the structure of stent 102 interfering with blood flow to the coronary arteries. At least partly due to the shape of cells 112, stent 102 elongates in the direction of longitudinal axis L as the cells collapse when the stent transitions from the expanded condition to the collapsed condition, and shortens in the direction of longitudinal axis L as the stent transitions from the collapsed condition to the expanded condition.

Stent 102 may include one or more retaining elements 118 at outflow end 132, the retaining elements being sized and shaped to cooperate with retaining structures provided on a deployment device (not shown). The engagement of retaining elements 118 with the retaining structures on the deployment device may help maintain prosthetic heart valve 100 in assembled relationship with the deployment device, minimize longitudinal movement of the prosthetic heart valve relative to the deployment device during unsheathing or resheathing procedures, and help prevent rotation of the prosthetic heart valve relative to the deployment device as the deployment device is advanced to the target location and during deployment. One such deployment device is described in U.S. Patent Publication No. 2012/0078352, the entire contents of which are hereby incorporated by reference herein.

Stent 102 may also include a plurality of commissure attachment features 116 for mounting the commissures of the valve assembly to the stent. As can be seen in FIG. 1, each commissure attachment feature 116 may lie at the intersection of four cells 112, two of the cells being adjacent one another in the same annular row, and the other two cells being in different annular rows and lying in end-to-end relationship. Commissure attachment features 116 may be positioned entirely within annulus section 140 or at the juncture of annulus section 140 and transition section 141, and may include one or more eyelets or apertures which facilitate the suturing of the leaflet commissures to stent 102. Stent 102 may be formed as a unitary structure, for example, by laser cutting or etching a tube of a superelastic and/or shape-memory metal alloy, such as a nickel-titanium alloy of the type sold under the designation nitinol. Such a unitary structure may be referred to as a "non-woven" structure in that it is not formed by weaving or winding one or more filaments.

Prosthetic heart valve 100 includes a valve assembly 104 positioned in the annulus section 140 of stent 102. Valve assembly 104 includes a plurality of leaflets 108 that collectively function as a one way valve by coapting with one another, and a cuff 106 positioned on the luminal surface of stent 102 surrounding leaflets 108. As prosthetic heart valve 100 is intended to replace the aortic valve (which ordinarily is a tri-leaflet valve), it is shown in FIG. 1 with three leaflets 108. Adjacent leaflets 108 join one another at leaflet commissures. Each of the leaflet commissures may be sutured to a respective one of the three commissure attachment features 116. Between the leaflet commissures, each leaflet 108 may be sutured to stent 102 and/or to cuff 106 along a leaflet belly B, indicated with broken lines in FIG. 1. Leaflets 108 may be joined to stent 102 and/or to cuff 106 by techniques known in the art other than suturing. Above belly B, leaflets 108 are free to move radially inward to coapt with one another along their free edges. When prosthetic heart valve 100 is implanted in the native aortic valve annulus, blood flows in an antegrade direction from inflow end 130, past leaflets 108, and toward outflow end 132. This occurs when the pressure in the left ventricle is greater than the pressure in the aorta, forcing leaflets 108 to open. When the pressure in the aorta is greater than the pressure in the left ventricle, leaflets 108 are forced closed and coapt with one another along their free edges, blocking blood from flowing through prosthetic heart valve 100 in a retrograde direction from outflow end 132 to inflow end 130. It will be appreciated that prosthetic heart valves according to aspects of the present disclosure may have more or less than the three leaflets 108 and commissure attachment features 116 shown in FIG. 1 and described above.

Although cuff 106 is shown in FIG. 1 as being disposed on the luminal or inner surface of annulus section 140, the cuff may be disposed on the abluminal or outer surface of the annulus section, or may cover all or part of either or both of the luminal and abluminal surfaces of the annulus section. Cuff 106 may be scalloped at the inflow end 130 of stent 102, and may have a zig-zag structure at its outflow end, following certain stent struts 114 up to commissure attachment features 116 and other stent struts closer to the inflow end of the stent at circumferential positions between the commissure attachment features. As is shown in FIG. 1, in one example, the entirety of valve assembly 104, including the leaflet commissures, is positioned in the annulus section 140 of stent 102. When open, leaflets 108 may remain substantially completely within annulus section 140, or they may be designed to extend into transition section 141. In the embodiment shown, substantially the entirety of valve assembly 104 is positioned between the inflow end 130 of stent 102 and commissure attachment features 116, and none of the valve assembly is positioned between the commissure attachment features and the outflow end 132 of the stent.

In operation, prosthetic heart valve 100 described above may be used to replace a native heart valve, such as the aortic valve; a surgical heart valve; or a heart valve that has undergone a surgical procedure. Prosthetic heart valve 100 may be delivered to the desired site (e.g., near the native aortic annulus) using any suitable delivery device. During delivery, prosthetic heart valve 100 is disposed inside the delivery device in the collapsed condition. The delivery device may be introduced into the patient using any known percutaneous procedure, such as a transfemoral, transapical, or transseptal delivery procedure. Once the delivery device has reached the target site, the user may deploy prosthetic heart valve 100. Upon deployment, prosthetic heart valve 100 expands into secure engagement within the native aortic annulus. When prosthetic heart valve 100 is properly positioned inside the heart, it works as a one-way valve, allowing blood to flow in one direction and preventing blood from flowing in the opposite direction.

Figure 2:
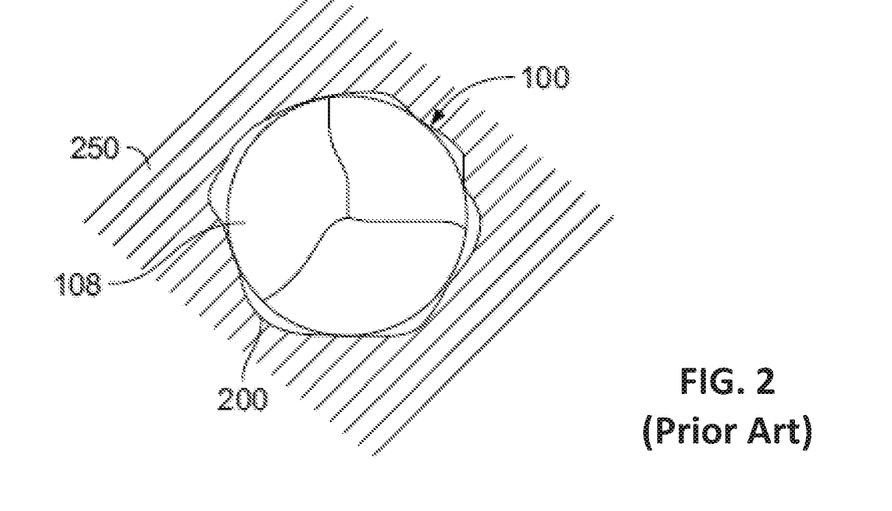
FIG. 2 is a highly schematic transverse cross-sectional view of the prior art prosthetic heart valve implanted in a patient, taken along line 2-2 of FIG. 1.

FIG. 2 is a highly schematic transverse cross-sectional illustration taken along line 2-2 of FIG. 2 and showing prosthetic heart valve 100 with leaflets 108 disposed within native valve annulus 250. As can be seen, the substantially circular annulus section 140 of stent 102 is disposed within a non-circular native valve annulus 250. At certain locations around the perimeter of prosthetic heart valve 100, gaps 200 are formed between the heart valve and native valve annulus 250. Retrograde blood flow through these gaps and around the outside of the valve assembly 104 of prosthetic heart valve 100 can result in PV leak or regurgitation and other inefficiencies which can reduce cardiac performance. Such improper fitment may be due to suboptimal native valve annulus geometry, for example, as a result of the calcification of the tissue of native valve annulus 250 or the presence of unresected native leaflets.

Figure 3A:
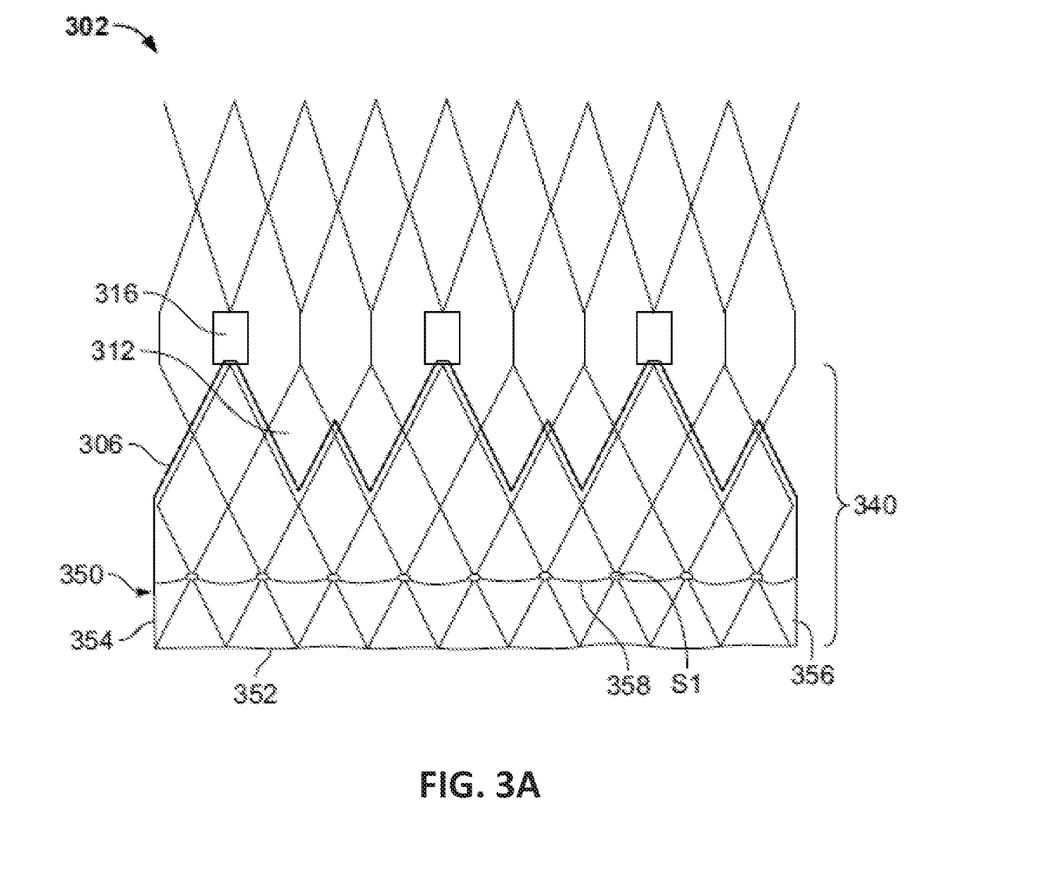
FIG. 3A is a schematic developed view of a stent with an outer cuff in an expanded condition according to an embodiment of the disclosure.
Figure 3B:
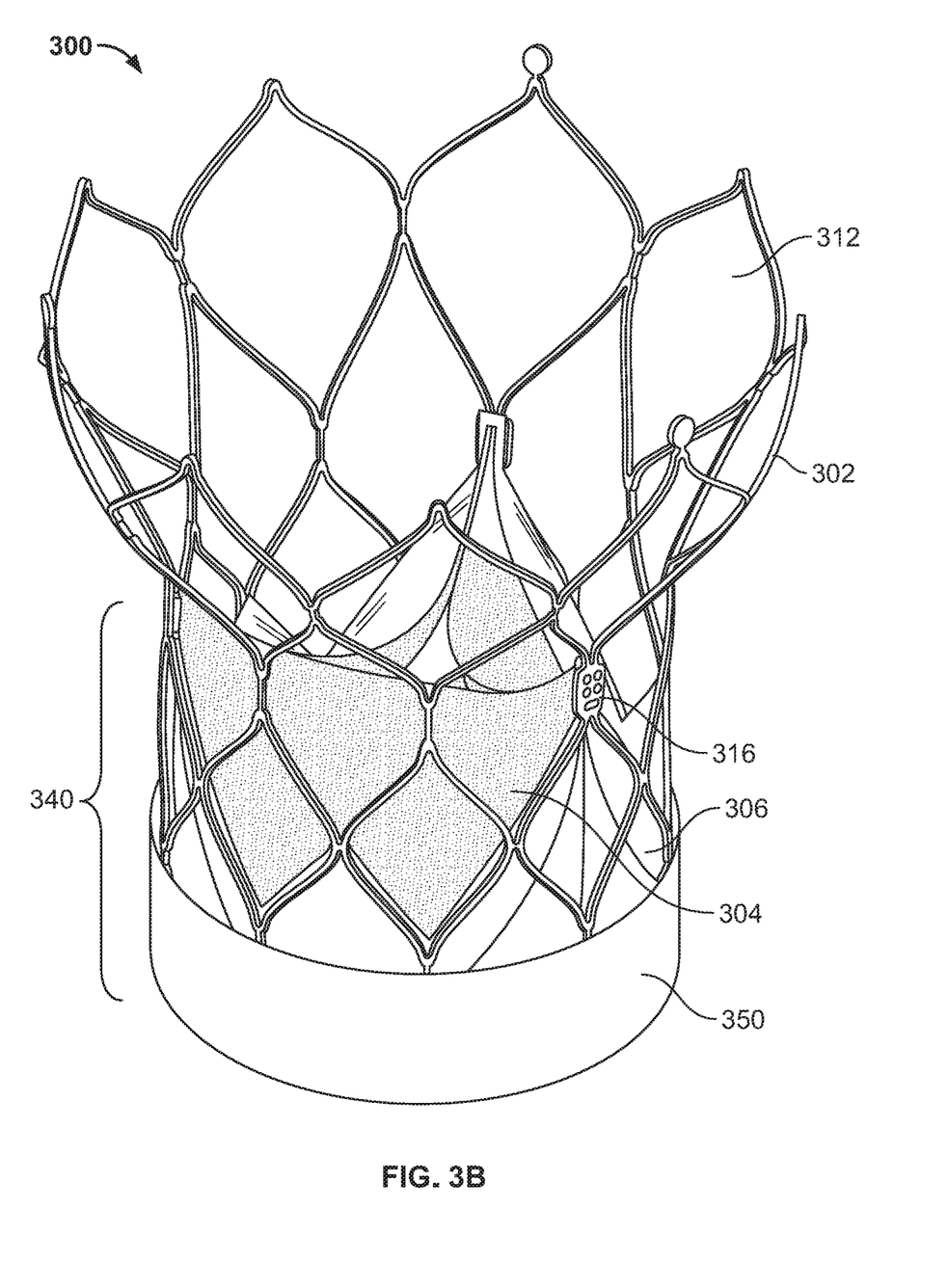
FIG. 3B is a perspective view of a prosthetic heart valve having the stent and outer cuff of FIG. 3A.

FIG. 3A illustrates the stent 302 of a prosthetic heart valve according to an aspect of the disclosure. FIG. 3B illustrates a prosthetic heart valve 300 that includes the stent 302 of FIG. 3A. Stent 302 may be similar or identical to stent 102 described above, with certain exceptions. For example, the annulus section 340 of stent 302 may include three rows of cells 312 instead of two rows, although in some embodiments stent 302 may include only two rows of cells in the annulus section, or any other number of rows of cells. Although commissure attachment features 316 of stent 302 are illustrated schematically as open rectangles in FIG. 3A, the commissure attachment features may have a form similar to commissure attachment features 116 shown in FIG. 1, or any other suitable form having any number of rows or columns of eyelets and/or eyelets of different sizes and/or shapes positioned in any arrangement on the commissure attachment feature. For example, as shown in FIG. 3B, commissure attachment features 116 may include a single elongated eyelet on a proximal end portion of the commissure attachment feature, with two rows and two columns of substantially rectangular-shaped eyelets positioned distally of the elongated eyelet. A cuff 306 similar or identical to cuff 106 may be positioned on the luminal and/or abluminal surface of stent 302. Rather than a scalloped inflow end as with cuff 106, however, cuff 306 may have a straight inflow end. As shown in FIG. 3B, prosthetic heart valve 300 may include a valve assembly 304 having a plurality of leaflets, similar or identical to valve assembly 104, positioned radially inwardly of cuff 306 and attached to that cuff.

In order to help minimize or eliminate PV leak, for example through the gaps 200 shown in FIG. 2, additional material may be coupled to the exterior of stent 302 as an outer cuff 350. In the illustrated example, outer cuff 350 may have a substantially rectangular shape and may be wrapped around the circumference of stent 302 at the inflow end of the stent so as to overlap in the longitudinal direction of the stent with cuff 306. Outer cuff 350 may be a single piece of material having a proximal edge 352, two side edges 354, 356, and a distal edge 358. Preferably, the proximal edge 352 of outer cuff 350 is coupled to stent 302 and/or to inner cuff 306 at or near the inflow end of the stent, for example by a continuous line of sutures (not shown), with the side edges 354 and 356 of the outer cuff joined to one another so that retrograde blood flow entering the space between the outer cuff and the inner cuff cannot pass in the retrograde direction beyond the combined cuffs. In order to allow retrograde blood flow to enter the space between outer cuff 350 and inner cuff 306, the distal edge 358 of the outer cuff may be attached to stent 302 and/or to inner cuff 306 at locations that are spaced apart in the circumferential direction. The distal edge 358 of outer cuff 350 may, for example, be sutured to stent 302 at attachment points S1 located where each cell 312 in the proximalmost row of cells intersects with an adjacent cell in that same row. In the illustrated example, since there are nine cells 312 in the proximalmost row, there are nine separate attachment points S1 at which the distal edge 358 of outer cuff 350 is sutured or otherwise attached to stent 302. Retrograde blood flow around the abluminal surface of stent 302 may enter the pocket or space between outer cuff 350 and inner cuff 306 via the spaces between adjacent attachment points S1. Once retrograde blood flow enters this space, outer cuff 350 may tend to billow outwardly, helping to fill any of gaps 200 between the prosthetic heart valve and native valve annulus 250. Although the foregoing description uses the term "inner" in connection with cuff 306, that is merely intended to indicate that cuff 306 is positioned radially inward of outer cuff 350. Inner cuff 306 may be located either on the luminal or abluminal side of stent 302, or on both sides.

Although described as a single piece of material above, outer cuff 350 may comprise multiple pieces of material that, when joined together, form a similar shape and provide similar function as described above for the outer cuff. Also, rather than being formed of a single substantially rectangular piece of material that is wrapped around the circumference of stent 302, outer cuff 350 may be formed as a continuous annular web without side edges 354, 356. Preferably, outer cuff 350 has an axial height measured from its proximal edge 352 to its distal edge 358 that is approximately half the axial height of a cell 312 in the proximalmost row of cells in stent 302 as measured along the major axis of the cell between two of its apices when the cell is in an expanded condition. However, outer cuff 350 may have other suitable heights, such as the full axial height of a cell 312 in the proximalmost row of cells, or more or less than the full axial height of a cell 312 in the proximalmost row of cells. Still further, although inner cuff 306 and outer cuff 350 are described above as separate pieces of material joined to stent 302 and to each other, the cuffs may be formed integrally with one another from a single piece of material that is wrapped around the proximal edge of the stent, with the distal edge 358 of the outer portion of the cuff joined to the stent and/or to the inner portion of the cuff at attachment points S1 as described above. With this configuration, the proximal edge 352 of outer cuff 350 does not need to be sutured to stent 302, although it still may be preferable to provide such attachment. Inner cuff 306 and outer cuff 350 may be formed of the same or different materials, including any suitable biological material or polymer such as, for example, polytetrafluoroethylene (PTFE), ultra-high molecular weight polyethylene (UHMWPE), polyurethane, polyvinyl alcohol, silicone, or combinations thereof.

Figure 4A:
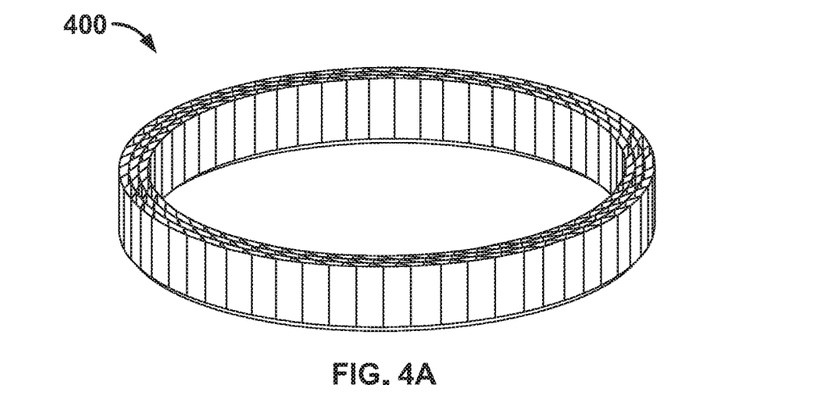
FIG. 4A is a perspective view of a filler for use with the heart valve of FIG. 3B.

For outer cuff 350 of prosthetic heart valve 300 to effectively mitigate PV leak, blood flowing in the retrograde direction around the outside of stent 302 preferably is readily able to enter the space between the outer cuff and inner cuff 306. Although the pressure prevailing during ventricular diastole may facilitate the movement of outer cuff 350 radially away from inner cuff 306 to provide an opening therebetween through which retrograde blood may flow, causing the outer cuff to billow outwardly to thus provide additional sealing, additional structures may be provided to assist the outer cuff to move radially away from the inner cuff to facilitate mitigation of PV leak. For example, FIG. 4A illustrates an expandable filler 400 that may be used in combination with prosthetic heart valve 300 in order to help ensure that, during operation of the prosthetic heart valve, outer cuff 350 is able to move radially away from inner cuff 306 to provide an opening between the inner and outer cuffs into which retrograde blood may flow.

Filler 400 preferably has a ring or annulus shape, and may include one or more layers in a radially stacked configuration. In the illustrated embodiment, filler 400 includes three layers 410a-c, although it should be understood that in other embodiments, the filler may include a single layer, two layers, or more than three layers. Each layer 410a-c may include a plurality of individual cells 420a-c extending circumferentially around the respective layer. Layer 410a may include an inner wall 430a and an outer wall 440a positioned radially outward of the inner wall. Layers 410b-c may similarly include inner walls 430b-c and outer walls 440b-c. Radially adjacent layers may include walls that are common to one another, or that are formed separately and then joined together. For example, outer wall 440a of layer 410a may be the same structure as inner wall 430b of layer 410b, or alternately they may be separate structures that are joined together. Each layer 410a-c may include a plurality of ribs 450a-c extending from the respective inner walls 430a-c to the respective outer walls 440a-c. Each cell 420a-c is bounded by a respective inner wall 430a-c, a respective outer wall 440a-c, and two respective ribs 450a-c that are adjacent one another. In the illustrated embodiment, the top or outflow end of each cell 420a-c is open, and the bottom or inflow end of each cell is open, although in other embodiments described in greater detail below, the inflow and/or outflow ends of each cell may be closed.

Figure 4B:
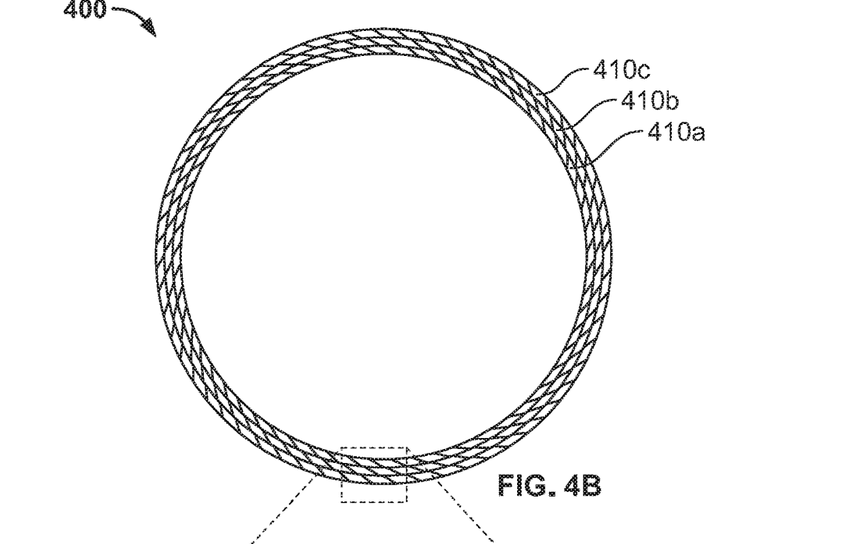
FIG. 4B is a transverse cross-section of the filler of FIG. 4A.
Figure 4C:
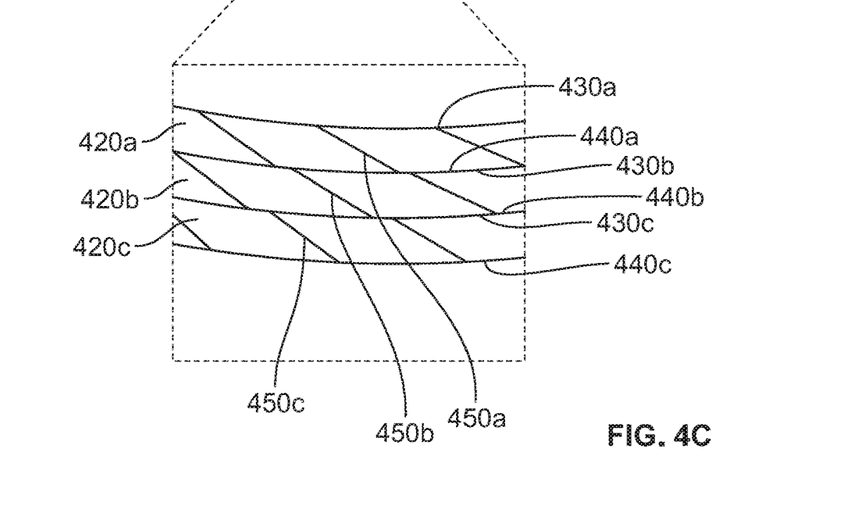
FIG. 4C is an enlarged cross-section of a portion of the filler of FIG. 4B.

Preferably, in the absence of applied force, filler 400 is in an expanded condition such as that shown in FIGS. 4B-C. When a radially constraining or compressing force is applied to filler 400, it may transition to a collapsed condition. In the collapsed condition, the outer wall 440a-c of each layer 410a-c is positioned closer in the radial direction to its corresponding inner wall 430a-c, reducing the radial distance between the inner wall of the innermost layer and the outer wall of the outermost layer. During the transition from the expanded condition to the collapsed condition, the angle between ribs 450a-c and the corresponding inner walls 430a-c and outer walls 440a-c decreases. In the illustrated embodiment, each cell 420a-c has the shape in transverse cross-section of a parallelogram, although it should be understood that a perfect parallelogram shape is not necessary, and still other shapes may be suitable. For example, in other embodiments, cells 420a-c may have the shape in cross-section of hexagons, diamonds, or other readily collapsible shapes.

In one example, filler 400 may be formed of an elastomeric material, such as a polyurethane-silicone copolymer. Other suitable materials for filler 400 include, but are not limited to, poly (styrene-b-isobutylene-b-styrene) and silicone. The elasticity of filler 400 may aid the filler to tend to be in the expanded condition in the absence of constraining forces. In other words, if filler 400 is constrained into the collapsed condition, the elasticity of the material forming the filler may cause the filler to transition to the expanded condition upon removal of the constraint. Depending on the particular material chosen for filler 400, and the strength of that material, inner walls 430a-c, outer walls 440a-c, and ribs 450a-c may each have a small thickness. For example, certain polyurethane-silicone polymers may provide enough strength so that the inner walls 430a-c, outer walls 440a-c, and ribs 450a-c may each have a small thickness. Minimizing the thickness of inner walls 430a-c, outer walls 440a-c, and ribs 450a-c is preferable in order to help maintain a small profile when filler 400 and prosthetic heart valve 300 are transitioned to a collapsed condition for delivery into a patient. However, it will be understood that it is also preferable that inner walls 430a-c, outer walls 440a-c, and ribs 450a-c are strong enough to return to the expanded condition after being released from a constraint keeping filler 400 in the collapsed condition. That strength may be determined at least in part by the thickness of inner walls 430a-c, outer walls 440a-c, and ribs 450a-c, as well as by the material properties of the particular material forming filler 400. It should further be understood that the overall thickness of filler 400 may be increased, if desired, by adding additional layers, increasing the length of ribs 450a-c, and/or increasing the thickness of inner walls 430a-c and/or outer walls 440a-c.

In order to help filler 400 maintain a relatively small profile in the collapsed condition, it is preferable that the vertices of the cells 420a-c in one of layers 410a-c be offset in the circumferential direction from the vertices of the cells in any of the other layers. That is, because the thickness of the cell vertices may be greater than the thicknesses of inner walls 430a-c, outer walls 440a-c, and ribs 450a-c, it is desirable that the vertices do not overlie one another in the radial direction of filler 400. For example, each rib 450a has one point of connection to outer wall 440a of layer 410a and another point of connection to inner wall 430a of layer 410a, each of which may be referred to as a vertex of a corresponding cell 420a. Similarly, each rib 450b has a point of connection to outer wall 440b of layer 410b and a point of connection to inner wall 430b of layer 410b, each of which may be referred to as a vertex of a corresponding cell 420b. Preferably, these two sets of vertices are offset from one another in the circumferential direction so that they do not overlie one another in the radial direction of filler 400. In other words, a radius line drawn from the center of filler 400 to the outermost layer 410c of the filler preferably will not extend through a vertex of a cell 420a in layer 410a and a cell 420b in layer 410b. More preferably, such radius line also will not extend through a vertex of a cell 420c in layer 410c. Since filler 400 may have a slightly greater thickness at these vertices, staggering the vertices in the circumferential direction so that they do not overlie one another in the radial direction may help reduce the profile of the filler in the collapsed condition compared to a similar filler that includes radially aligned vertices. Still more preferably, the points of connection of ribs 450a with outer wall 440a are positioned equidistantly between the points of connection of connecting ribs 450b with inner wall 430b. The points of connections of ribs 450b with outer wall 440b are preferably similarly staggered or offset in the circumferential direction relative to the points of connection of ribs 450c with inner wall 430c. If additional layers are included in filler 400, it is preferable that this pattern continues so that the ribs of radially adjacent layers do not have radially overlapping points of connection, or that any such overlap is minimized.

As noted above, filler 400 may be positioned between outer cuff 350 and stent 302 of prosthetic heart valve 300. The height of filler 400 from the proximal (or inflow) end to the distal (or outflow) end may be about equal to the height of outer cuff 350 between proximal edge 352 and distal edge 358 so that the filler may completely fill the space between the outer cuff and the ablumenal surface of stent 302. In other embodiments, the proximal-to-distal height of filler 400 may be smaller than the proximal-to-distal height of outer cuff 350 so that the filler only partially fills the space between the outer cuff and the ablumenal surface of stent 302. Filler 400 may be attached to stent 302, inner cuff 306, and/or outer cuff 350 in any suitable manner, including sutures, adhesives, heat setting/curing, and overmolding. Further, when using filler 400 with prosthetic heart valve 300, it may be preferable that the distal edge 358 of outer cuff 350 is attached only to filler 400, and not to stent 302 or inner cuff 306. With this attachment configuration, the entire length of the distal edge 358 of outer cuff 350 may be spaced a distance apart in the radial direction from inner cuff 306 and stent 302, maximizing the area for retrograde blood to flow into the space between the outer cuff and the inner cuff and/or stent. However, in other embodiments, outer cuff 350 may be attached to stent 302 and/or inner cuff 306 as shown in FIG. 3A with sutures at attachment points S1.

In operation, prosthetic heart valve 300, with filler 400 positioned between outer cuff 350 and inner cuff 306, may be transitioned into a collapsed condition and loaded onto a delivery device for delivery into a patient. Prosthetic heart valve 300 may be advanced to the aortic valve of the patient while it is maintained in the collapsed condition, for example by an overlying sheath of the delivery device that radially constrains the prosthetic heart valve. Once at the desired location, such as the native aortic valve, the overlying sheath may be removed from prosthetic heart valve 300, removing the constraining force. In the absence of any constraining forces, prosthetic heart valve 300, along with filler 400, returns to the expanded condition. As filler 400 expands, it may push outer cuff 350 radially outwardly into any gaps between prosthetic heart valve 300 and the native aortic annulus. During normal operation, if any blood flows in the retrograde direction around the outside of stent 302, that blood may flow into the space between outer cuff 350 and inner cuff 306, with filler 400 helping to maintain an opening between the distal edge 358 of the outer cuff and the inner cuff. Blood flowing into the space between inner cuff 306 and outer cuff 350 may result in the outer cuff billowing outwardly to some degree to further seal any remaining spaces between prosthetic heart valve 300 and the native aortic valve annulus, helping to mitigate or eliminate PV leak.

In the illustrated embodiment, when filler 400 is positioned between outer cuff 350 and inner cuff 306 of prosthetic heart valve 300, the proximal and distal ends of the filler may remain open so that a channel extends through each cell 420a-c from the proximal end to the distal end. If blood does flow into the space between inner cuff 306 and outer cuff 350 during operation, that blood may flow through the channels in cells 420a-c, which may help to further expand filler 400 radially outwardly. At least because the proximal edge 352 of outer cuff 350 is coupled to inner cuff 306, blood entering the space between the outer cuff and inner cuff is trapped within that volume.

Figure 5A:
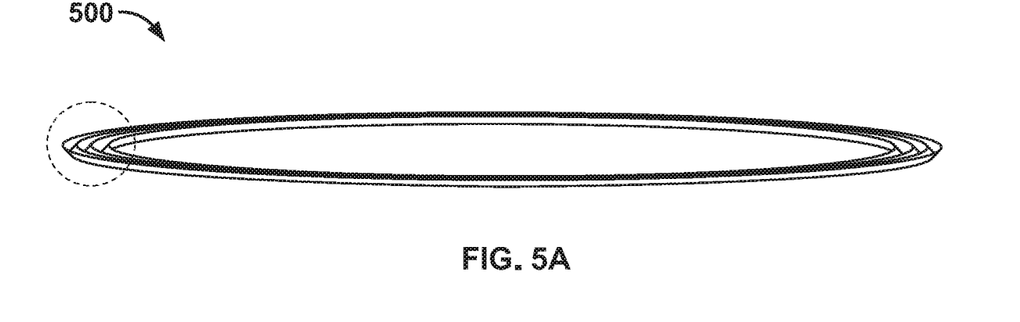
FIG. 5A is a top perspective view of an end cap for use with the filler of FIG. 4A.
Figure 5B:
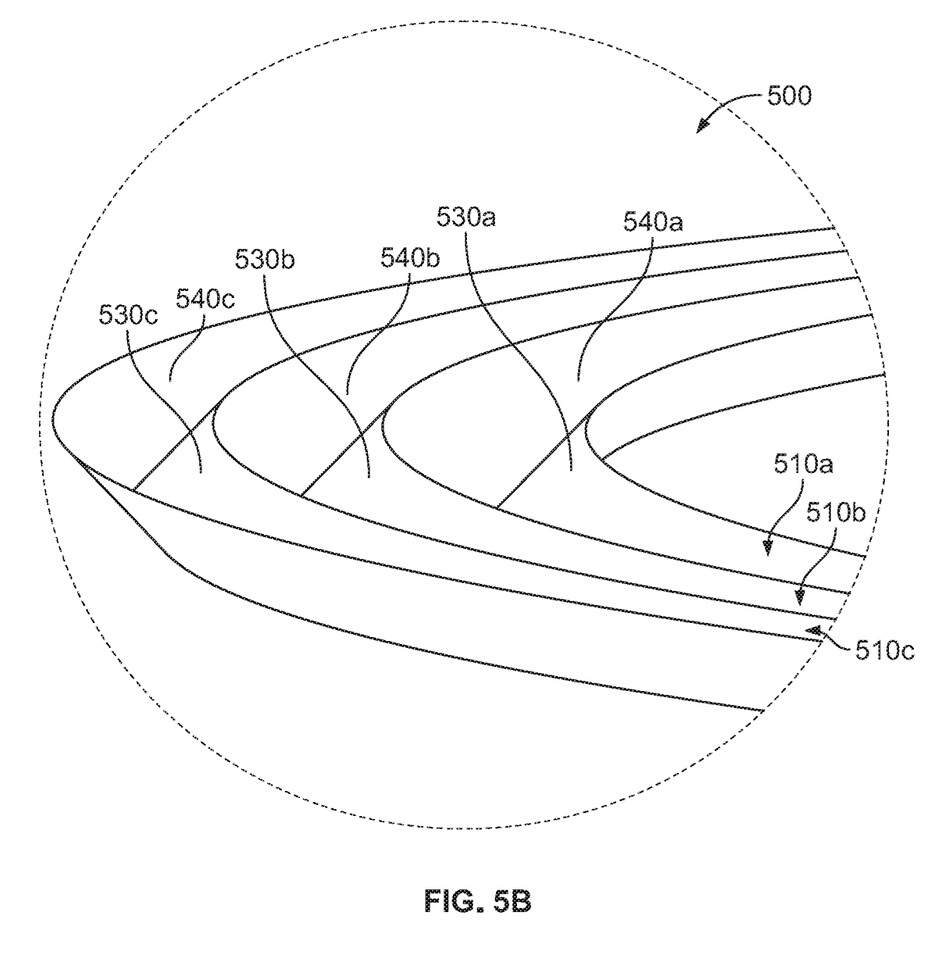
FIG. 5B is an enlarged perspective view of a portion of the end cap of FIG. 5A.
Figure 5C:
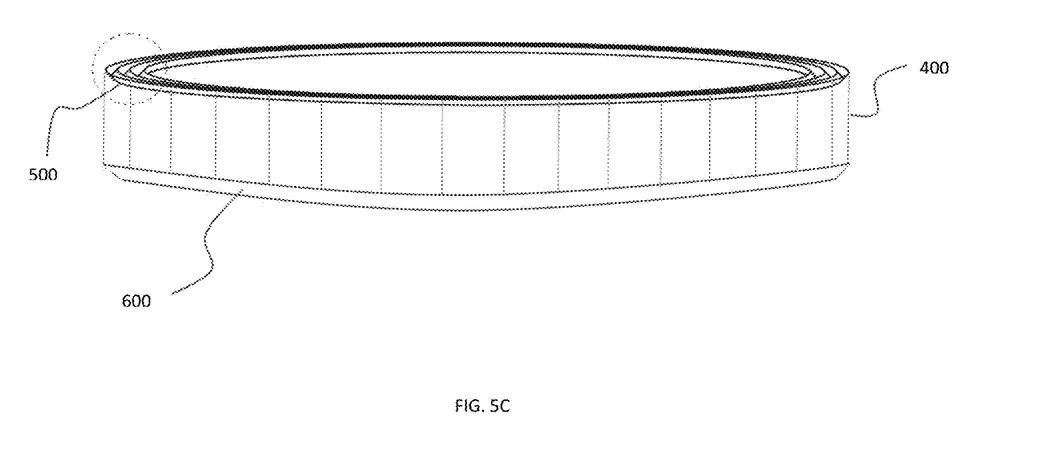
FIG. 5C is a front perspective view of a filler with two end caps, according to an embodiment of the disclosure.

FIG. 5A is a perspective view of an end cap 500 that may be used with filler 400 to close the proximal and/or distal ends of the filler. FIG. 5B shows an enlarged portion of end cap 500. End cap 500 may be particularly suited for use with filler 400 in conjunction with a prosthetic heart valve that is similar or identical to prosthetic heart valve 300, but without an outer cuff 350. However, as will be described in greater detail below, one or two end caps 500 may be coupled to filler 400 even if the filler is used in conjunction with a prosthetic heart valve having an outer cuff 350. FIG. 5C shows the filler 400 with an end cap 500 at the proximal end and an end cap 600 at the distal end.

End cap 500 may be generally annular or ring shaped and have expanded and collapsed conditions. In the illustrated embodiment, end cap 500 includes a first innermost ring-shaped channel 510a, a second ring-shaped channel 510b positioned radially outwardly of the first channel, and a third ring-shaped channel 510c positioned radially outwardly of the first and second channels. Each channel 510a-c may be formed from an inner wall 530a-c and an outer wall 540a-c. Channels 510a-c may each have a longitudinal cross-sectional shape of a "V," a half-diamond, or another shape that allows the inner wall 530a-c of a channel to collapse toward the corresponding outer wall 540a-c of the channel. Each inner wall 530a-c may be coupled to the corresponding outer wall 540a-c of the same channel 510a-c so that blood is unable to pass across the areas where the inner walls are attached to the outer walls, for example at the vertex of the "V"-shape.

One or two end caps 500 may be coupled to filler 400. In the illustrated example, end cap 500 includes the same number of channels 510a-c as the number of layers 410a-c of filler 400. With this configuration, an end cap 500 may be coupled to either the proximal or distal end of filler 400 so that inner walls 530a-c align with corresponding inner walls 430a-c, and outer walls 540a-c align with corresponding outer walls 440a-c. If a single end cap 500 is coupled to the proximal end of filler 400, retrograde blood flow into the distal end of filler 400 will pass through cells 420a-c of layers 410a-c and into corresponding channels 510a-c, with end cap 500 limiting or preventing that blood from passing back through the native valve annulus.

If filler 400 is coupled to a prosthetic heart valve that is identical to prosthetic heart valve 300 but without an outer cuff 350, it is preferable to couple a first end cap 500 to the proximal end of filler 400. With this configuration, the prosthetic heart valve may be loaded into a delivery device and deployed at the native heart valve annulus in the same manner as described above, with filler 400 expanding into any gaps between the prosthetic heart valve and the native valve annulus. It should be understood that filler 400 is preferably sufficiently pliable to conform to the shape of the native valve annulus. During retrograde flow of blood around the outside of the prosthetic heart valve, blood may flow into cells 420a-c through the distal end of filler 400. The blood flow may cause filler 400 to further expand, with end cap 500 ensuring that the blood does not exit the proximal end of the filler. Rather than leave the distal end of filler 400 open, a second end cap 500 may be coupled to the distal end of the filler so that both the proximal and distal ends of the filler are sealed. In such arrangement, retrograde blood flow around the outside of the prosthetic heart valve will not enter the cells 420a-c of the filler. If the expansion of filler 400 is sufficient to seal any gaps existing between the prosthetic heart valve and the native valve annulus, the ability of blood to enter cells 420a-c may not confer a significant additional benefit. On the other hand, there may be a risk that contact of blood with the relatively large surface area of inner walls 430a-c, outer walls 440a-c, and ribs 450a-c may result in thrombus formation. By sealing the proximal and distal ends of filler 400 with end caps 500, blood will not enter cells 420a-c, reducing or eliminating the risk of thrombus formation by contact of blood with the interior space of the filler. As noted above, end caps 500 may be positioned on both the proximal and distal ends of filler 400 even when used in combination with an outer cuff 350. That particular embodiment may similarly reduce the likelihood of thrombus formation by reducing or eliminating the contact between blood and the interior structures of filler 400, with the filler still helping to push outer cuff 350 radially outwardly to help seal against PV leak. If desired, a single end cap 500 may be used with filler 400 in conjunction with a prosthetic valve having an outer cuff 350, either on the proximal or distal end of the filler.

In some embodiments, end cap 500 may be coupled to the proximal and/or distal ends of filler 400 by any suitable method including, for example, sutures, adhesives, heat setting/curing, and overmolding. In other embodiments, end cap 500 may be formed integrally with filler 400, such that the end cap does not need to be separately attached to the filler. End cap 500 may be made from any suitable material, including those mentioned above in connection with filler 400. In some embodiments, filler 400 and end cap 500 both may be made from the same material as one another. In embodiments in which end cap 500 has the same number of channels 510a-c as filler 400 has layers 410a-c, it may be preferable that the end cap is coupled to the filler so that each channel of the end cap remains aligned with a corresponding layer of the filler as the assembly is expanded or contracted. However, it should be understood that end cap 500 need not have a number of channels 510a-c equal to the number of layers 410a-c of filler 400. For example, end cap 500 may have more or fewer channels than the number of layers of filler 400. Rather, end cap 500 preferably includes structures that allow for its connection to filler 400 in a manner that seals the filler against blood entering (or exiting) the filler where the end cap is attached, and that further allow for the end cap to collapse and expand along with the filler.

It should be understood that although filler 400 and optional end cap(s) 500 are described in connection with a prosthetic aortic valve, the same or similar items may be used in conjunction with a prosthetic heart valve for implantation into the mitral valve, the tricuspid valve, or the pulmonary valve.

In addition, although the term "filler" is used herein to describe certain structures that may help to fill certain space between a prosthetic heart valve and adjacent native tissue when implanted, or otherwise to fill space between an inner and an outer cuff of a prosthetic heart valve, the term "filler" itself is not limited to any particular structure or particular function. In other words, according to one aspect of the disclosure, a "filler" is described as having a first circumferential layer with a first inner wall, a first outer wall, and a plurality of first ribs connecting the first inner wall to the first outer wall. It should be understood that, in that particular example of a filler, any structure having a first circumferential layer with a first inner wall, a first outer wall, and a plurality of first ribs connecting the first inner wall to the first outer wall, may be considered a "filler." In addition, the term "filler" does not imply or require (i) that the "filler" structure be filled with anything, or (ii) that the "filler" structure functions to filler any other structure.

While filler 400 (with or without end cap 500) has been described herein in conjunction with prosthetic heart valve 300 that includes outer cuff 350, it should be understood that the filler (with or without the end cap) could be used in conjunction with a prosthetic heart valve without an outer cuff, such as prosthetic heart valve 100. Still further, filler 400 (with our without end cap 500) could be used in conjunction with various other collapsible prosthetic heart valves, including, for example, those described in U.S. Pat. Nos. 8,808,356 and/or 8,425,593 and/or U.S. Patent Publication No. 2018/0055631 and/or U.S. Patent Publication No. 2018/0116798, the disclosures of which are each hereby incorporated by reference herein.

According to a first aspect of the disclosure, a prosthetic heart valve for replacing a native valve comprises:

a stent extending in a longitudinal direction from an inflow end to an outflow end and having a plurality of stent cells formed by struts, a collapsed condition and an expanded condition;

a valve assembly disposed within the stent;

a first cuff annularly disposed adjacent the stent; and a filler annularly disposed about the stent radially outward of the first cuff and radially outward of the stent, the filler having a first circumferential layer with a first inner wall, a first outer wall, and a plurality of first ribs connecting the first inner wall to the first outer wall, wherein the filler has an expanded condition in which the first inner wall is spaced a first distance from the first outer wall in a radial direction transverse to the longitudinal direction of the stent, and a collapsed condition in which the first inner wall is spaced a second distance from the first outer wall in the radial direction, the first distance being greater than the second distance; and/or the filler extends from a proximal end to a distal end, the proximal end of the filler being positioned nearer the inflow end of the stent than is the distal end of the filler; and/or the first circumferential layer of the filler includes a plurality of first cells extending from the proximal end of the filler to the distal end of the filler; and/or each of the plurality of first cells is defined by the first inner wall, the first outer wall, and two adjacent ones of the plurality of first ribs; and/or in the expanded condition of the filler, each of the plurality of first cells has a shape of a parallelogram in transverse cross-section; and/or the filler has a second circumferential layer with a second inner wall, a second outer wall, and a plurality of second ribs connecting the second inner wall to the second outer wall, the second circumferential layer being positioned radially outward of the first circumferential layer; and/or the second inner wall of the second circumferential layer and the first outer wall of the first circumferential layer are integral with one another; and/or each first rib connects to the first outer wall of the first circumferential layer at a first connecting point, and each second rib connects to the second inner wall of the second circumferential layer at a second connecting point, each first connecting point being offset in a circumferential direction between a pair of adjacent second connecting points; and/or a second cuff having a proximal edge facing toward the inflow end of the stent and a distal edge facing toward the outflow end of the stent, the second cuff being annularly disposed about the stent radially outward of the filler; and/or the distal edge of the second cuff is coupled directly to the stent at a plurality of locations spaced apart from one another in a circumferential direction of the stent; and/or the distal edge of the second cuff is coupled directly to the filler at a plurality of locations spaced apart from one another in a circumferential direction of the filler; and/or the distal edge of the second cuff is not directly coupled to the stent; and/or a collapsible and expandable end cap positioned at the proximal end of the filler so that fluid entering the distal end of the filler between the first inner wall and second inner wall of the first circumferential layer is restricted from exiting the filler through the proximal end; and/or the end cap is integral with the filler; and/or the end cap has a first inner wall coupled to the first inner wall of the first circumferential layer of the filler, and a first outer wall coupled to the first outer wall of the first circumferential layer of the filler; and/or a second cuff having a proximal edge facing toward the inflow end of the stent and a distal edge facing toward the outflow end of the stent, the second cuff being annularly disposed about the stent radially outward of the filler, the first circumferential layer of the filler being in fluid communication with an outside of the filler via the distal end of the filler; and/or a collapsible and expandable first end cap positioned at the proximal end of the filler, and a collapsible and expandable second end cap positioned at the distal end of the filler, so that an interior of the first circumferential layer of the filler is not in fluid communication with an exterior of the filler; and/or the filler includes a radial outermost layer that is uncovered so that, upon implantation of the prosthetic heart valve in a native valve annulus, the radial outermost layer of the filler is configured to directly contact the native valve annulus; and/or a second cuff having a proximal edge facing toward the inflow end of the stent and a distal edge facing toward the outflow end of the stent, the second cuff being annularly disposed about the stent radially outward of the filler; and/or the first end cap and the second end cap are integral with the filler.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, features of one embodiment described above may be combined with features of other embodiments described above.

The invention claimed is:

1. A prosthetic heart valve for replacing a native valve, comprising:
   a stent extending in a longitudinal direction from an inflow end to an outflow end and having a plurality of stent cells formed by struts, a collapsed condition and an expanded condition;
   a valve assembly disposed within the stent;
   an inner cuff annularly disposed adjacent the stent;
   a filler having a first length along the longitudinal direction and annularly disposed about the stent radially outward of the inner cuff and radially outward of the stent, the filler having a first circumferential layer with a first inner wall having a second length along the longitudinal direction, a first outer wall having a third length along the longitudinal direction, and a plurality of first ribs connecting the first inner wall to the first outer wall, wherein the second length and the third length are coextensive of the first length;
   a collapsible and expandable end cap positioned at the proximal end of the filler so that fluid entering the distal end of the filler between the first inner wall and first outer wall of the first circumferential layer is restricted from exiting the filler through the proximal end; and
   an outer cuff having a proximal edge facing toward the inflow end of the stent and a distal edge facing toward the outflow end of the stent, the outer cuff being annularly disposed about the stent radially outward of the filler, the first circumferential layer of the filler being in fluid communication with an outside of the filler via the distal end of the filler,
   wherein the filler has an expanded condition in which the first inner wall is spaced a first distance from the first outer wall in a radial direction transverse to the longitudinal direction of the stent, and a collapsed condition in which the first inner wall is spaced a second distance from the first outer wall in the radial direction, the first distance being greater than the second distance,
   wherein the prosthetic heart valve is configured to assume a collapsed condition in which the stent and the filler are in the respective collapsed conditions, and
   wherein the filler extends from a proximal end to a distal end, the proximal end of the filler being positioned nearer the inflow end of the stent than is the distal end of the filler.

2. The prosthetic heart valve of claim 1, further comprising a collapsible and expandable second end cap positioned at the distal end of the filler, so that an interior of the first circumferential layer of the filler is not in fluid communication with an exterior of the filler.

3. The prosthetic heart valve of claim 2, wherein the filler includes a radial outermost layer that is uncovered so that, upon implantation of the prosthetic heart valve in a native valve annulus, the radial outermost layer of the filler is configured to directly contact the native valve annulus.

4. The prosthetic heart valve of claim 2, wherein the first end cap and the second end cap are integral with the filler.

5. The prosthetic heart valve of claim 1, wherein the first circumferential layer of the filler includes a plurality of first cells extending from the proximal end of the filler to the distal end of the filler.

6. The prosthetic heart valve of claim 5, wherein each of the plurality of first cells is defined by the first inner wall, the first outer wall, and two adjacent ones of the plurality of first ribs.

7. The prosthetic heart valve of claim 5, wherein, in the expanded condition of the filler, each of the plurality of first cells has a shape of a parallelogram in transverse cross-section.

8. The prosthetic heart valve of claim 1, wherein the end cap is integral with the filler.

9. The prosthetic heart valve of claim 1, wherein the end cap has a first inner wall coupled to the first inner wall of the first circumferential layer of the filler, and a first outer wall coupled to the first outer wall of the first circumferential layer of the filler.

10. The prosthetic heart valve of claim 1, wherein the filler has a second circumferential layer with a second outer wall, and a plurality of second ribs connecting the first outer wall to the second outer wall, the second circumferential layer being positioned radially outward of the first circumferential layer.

11. The prosthetic heart valve of claim 10, wherein each first rib connects to the first outer wall of the first circumferential layer at a first connecting point, and each second rib connects to the first outer wall at a second connecting point, each first connecting point being offset in a circumferential direction between a pair of adjacent second connecting points.

12. The prosthetic heart valve of claim 1, further comprising an outer cuff having a proximal edge facing toward the inflow end of the stent and a distal edge facing toward the outflow end of the stent, the outer cuff being annularly disposed about the stent radially outward of the filler.

13. The prosthetic heart valve of claim 12, wherein the distal edge of the outer cuff is coupled directly to the stent at a plurality of locations spaced apart from one another in a circumferential direction of the stent.

14. The prosthetic heart valve of claim 12, wherein the distal edge of the outer cuff is coupled directly to the filler at a plurality of locations spaced apart from one another in a circumferential direction of the filler.

15. The prosthetic heart valve of claim 14, wherein the distal edge of the outer cuff is not directly coupled to the stent.

16. A prosthetic heart valve for replacing a native valve, comprising:
- a stent extending in a longitudinal direction from an inflow end to an outflow end and having a plurality of stent cells formed by struts, a collapsed condition and an expanded condition;
- a valve assembly disposed within the stent;
- an inner cuff annularly disposed adjacent the stent;
- a filler having a first length along the longitudinal direction and annularly disposed about the stent radially outward of the inner cuff and radially outward of the stent, the filler having a first circumferential layer with a first inner wall having a second length along the longitudinal direction, a first outer wall having a third length along the longitudinal direction, and a plurality of first ribs connecting the first inner wall to the first outer wall, wherein the second length and the third length are coextensive of the first length;
- a collapsible and expandable first end cap positioned at the proximal end of the filler, and a collapsible and expandable second end cap positioned at the distal end of the filler, so that an interior of the first circumferential layer of the filler is not in fluid communication with an exterior of the filler; and
- an outer cuff having a proximal edge facing toward the inflow end of the stent and a distal edge facing toward the outflow end of the stent, the outer cuff being annularly disposed about the stent radially outward of the filler,
- wherein the filler has an expanded condition in which the first inner wall is spaced a first distance from the first outer wall in a radial direction transverse to the longitudinal direction of the stent, and a collapsed condition in which the first inner wall is spaced a second distance from the first outer wall in the radial direction, the first distance being greater than the second distance,
- wherein the prosthetic heart valve is configured to assume a collapsed condition in which the stent and the filler are in the respective collapsed conditions, and
- wherein the filler extends from a proximal end to a distal end, the proximal end of the filler being positioned nearer the inflow end of the stent than is the distal end of the filler.

\* \* \* \* \*